US010696249B2

(12) United States Patent
Heinrich et al.

(10) Patent No.: US 10,696,249 B2
(45) Date of Patent: Jun. 30, 2020

(54) AUTOMATIC CAR SETTING ADJUSTMENTS BY IDENTIFYING DRIVER WITH HEALTH WATCH WEARABLE OR IN-CAR SENSORS

(71) Applicant: KONINKLIJKE PHILIPS N.V., Eindhoven (NL)

(72) Inventors: Adrienne Heinrich, Den Bosch (NL); Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 199 days.

(21) Appl. No.: 15/893,085

(22) Filed: Feb. 9, 2018

(65) Prior Publication Data

US 2018/0229674 A1 Aug. 16, 2018

Related U.S. Application Data

(60) Provisional application No. 62/457,512, filed on Feb. 10, 2017, provisional application No. 62/609,720, filed on Dec. 22, 2017.

(51) Int. Cl.
*B60R 16/023* (2006.01)
*B60K 28/06* (2006.01)
(Continued)

(52) U.S. Cl.
CPC ............ *B60R 16/0231* (2013.01); *A61B 3/11* (2013.01); *A61B 5/0205* (2013.01); *A61B 5/12* (2013.01); *A61B 5/18* (2013.01); *A61B 5/4552* (2013.01); *A61B 5/4803* (2013.01); *A61B 5/6893* (2013.01); *B60K 28/063* (2013.01); *B60R 16/037* (2013.01); *G05B 13/026* (2013.01); *G06K 9/00845* (2013.01); *G06K 9/00892* (2013.01); *A61B 5/02405* (2013.01); (Continued)

(58) Field of Classification Search
CPC . B60R 16/0231; B60R 16/037; B60K 29/063; A61B 3/11; A61B 5/0205; A61B 5/12; A61B 5/18; A61B 5/4552; A61B 5/4803; A61B 5/6893; A61B 5/0533; A61B 5/1172; A61B 5/1176; A61B 5/4806; A61B 5/02405; A61B 5/0531; A61B 5/08; A61B 5/1118; A61B 5/1171; G06K 9/00845; G06K 9/00892; G06K 9/00832; G06K 2009/00939; G06K 9/00221; G05B 13/026; G05B 13/0265; B60W 2540/22; B60W 2050/0082; B60W 2050/0089; B60W 2540/28
USPC .......................................................... 701/48
See application file for complete search history.

(56) References Cited

U.S. PATENT DOCUMENTS 6,831,993 B2 * 12/2004 Lemelson ............ B60Q 1/0023
307/10.5
8,398,546 B2 3/2013 Pacione
(Continued)

FOREIGN PATENT DOCUMENTS

| EP | 2891589 A2 | 7/2015 |
|---|---|---|
| WO | 2015084353 A1 | 6/2015 |
| WO | 2015084353 A1 | 7/2015 |

*Primary Examiner* — Muhammad Shafi (57) ABSTRACT

In one embodiment, a wearable device comprising one or more sensors is presented that receives one or more physiological parameters of a user sensed by the one or more sensors and causes adjustment of one or more vehicle parameters based on the one or more physiological parameters.

13 Claims, 4 Drawing Sheets

(51) Int. Cl.
    *A61B 3/11* (2006.01)
    *A61B 5/0205* (2006.01)
    *A61B 5/12* (2006.01)
    *A61B 5/18* (2006.01)
    *A61B 5/00* (2006.01)
    *G06K 9/00* (2006.01)
    *G05B 13/02* (2006.01)
    *B60R 16/037* (2006.01)
    *A61B 5/1172* (2016.01)
    *A61B 5/1171* (2016.01)
    *A61B 5/024* (2006.01)
    *A61B 5/053* (2006.01)
    *A61B 5/08* (2006.01)
    *A61B 5/11* (2006.01)
    *B60W 50/00* (2006.01)

(52) U.S. Cl.
    CPC ........... *A61B 5/0531* (2013.01); *A61B 5/0533* (2013.01); *A61B 5/08* (2013.01); *A61B 5/1118* (2013.01); *A61B 5/1171* (2016.02); *A61B 5/1172* (2013.01); *A61B 5/1176* (2013.01); *A61B 5/4806* (2013.01); *B60W 2050/0082* (2013.01); *B60W 2050/0089* (2013.01); *B60W 2540/043* (2020.02); *B60W 2540/22* (2013.01); *G05B 13/0265* (2013.01); *G06K 9/00221* (2013.01); *G06K 9/00832* (2013.01); *G06K 2009/00939* (2013.01)

(56) References Cited

U.S. PATENT DOCUMENTS

| | | | |
|---|---|---|---|
| 8,761,998 B2 | 6/2014 | Chen | |
| 9,418,491 B2 | 8/2016 | Phillips | |
| 9,682,711 B2* | 6/2017 | Lee | A61B 5/02427 |
| 2014/0253303 A1* | 9/2014 | Levesque | G06F 3/016 |
| | | | 340/407.1 |
| 2014/0341441 A1* | 11/2014 | Slaby | G06F 21/32 |
| | | | 382/117 |
| 2016/0264131 A1* | 9/2016 | Chan | B60W 30/025 |
| 2017/0140141 A1* | 5/2017 | Yan | G06F 21/316 |
| 2017/0355377 A1* | 12/2017 | Vijaya Kumar | B60W 40/08 |
| 2018/0109482 A1* | 4/2018 | DeLuca | G06N 20/00 |

\* cited by examiner

AUTOMATIC CAR SETTING ADJUSTMENTS BY IDENTIFYING DRIVER WITH HEALTH WATCH WEARABLE OR IN-CAR SENSORS

CROSS-REFERENCE TO RELATED APPLICATIONS

The present application claims priority to and benefit of U.S. Provisional Application No. 62/457,512, filed Feb. 10, 2017, and U.S. Provisional Application No. 62/609,720, filed Dec. 22, 2017, the entirety of which is hereby incorporated by reference herein.

FIELD OF THE INVENTION

The present invention is generally related to vehicles, and in particular, managing vehicle settings using sensors.

BACKGROUND OF THE INVENTION

A traditional car key opens a car door and allows the car to be driven (e.g., via ignition). Any adjustments (e.g., car seat, mirrors, temperature, radio channel, or other personal preferences) are performed manually. Based on recent technology, advancements have been made in creating vehicle amenities for users while also providing obstacles to unauthorized access to the vehicle, including the use of personal car keys that allow for the car seat to be adjusted automatically because a key is associated with one particular person whose preferences are stored. However, carrying a key is cumbersome. In U.S. Pat. No. 6,831,993 to Lemelson et al. (hereinafter, "Lemelson"), a facial-recognition system employing a camera directed at the face of a person in the driver's seat is disclosed, which system produces output control signals or codes that are applied to enable or disable operation of the vehicle, with or without use of a key or other supplemental security system (see, e.g., Summary of the Invention, Lemelson). The facial recognition may include an iris scan (see, e.g., claim 4 of Lemelson), and additional identification functionality may be deployed, including a fingerprint reading (see, e.g., claim 24 of Lemelson). In addition, the facial-recognition system is further coupled to an electronic control of the vehicle so as to alter a personal setting automatically based on code associated with the operator recognized by the facial-recognition system, said electronic control structured to control an operating setting of at least one of the following elements of the vehicle: (a) an audio system; (b) an electronic seat; (c) a window; (d) a temperature controller; (e) a mirror; and (f) the angle of the steering wheel column relative to the dashboard (see, e.g., claim 13 of Lemelson). The camera may be mounted on the front windshield frame, wind shield, or rear view mirror (see, e.g., Summary of the Invention, Lemelson). The camera may alternatively be mounted along a vertical center plane of the vehicle adjacent the rear window, with the scanning axis directed to the rear view mirror (see, e.g., claim 6 of Lemelson). Another extension of the system is to include the capability of storing data about the personal preferences of each authorized driver, which can be used to control automatically various powered options in the vehicle. For example, each driver's preferred seat position, cabin temperature, exterior mirror or window adjustments, angle of steering column, and music selection or volume can be stored. Upon recognition of the driver, the stored option signals for the recognized driver are applied to adjust those or other variables automatically. Certain recent-model automobiles have an electronically controlled seat-adjustment mechanism, for example, which save seat-location preferences of two or more different drivers, such as under "A" and "B" settings. It would be possible to couple such electronically controlled systems to the output of a personal-recognition system, so when the facial recognition system recognizes "driver A," a signal is sent to the known seat adjustment mechanism to put the seat in "position A." (see column 11, line 65+ of Lemelson).

Though adjusting the various vehicle device settings to the personal settings of the user based on facial recognition moves further away from the need for keys and aids in thwarting unlawful use of the vehicle, such a system also has some limitations inherent in a fixed camera system, including adaptability. For instance, the driver's settings are fixed, where change requires active participation by the driver to make adjustments.

SUMMARY OF THE INVENTION

One object of the present invention is to develop a vehicle settings adjustment system that is convenient to use and adaptable to changes in physiological parameters of a user. To better address such concerns, in a first aspect of the invention, a wearable device comprising one or more sensors is presented that receives one or more physiological parameters of a user sensed by the one or more sensors and causes adjustment of one or more vehicle parameters based on the one or more physiological parameters. The invention provides, among other features, a mechanism to monitor changes in the physiological parameters and adjust the vehicle parameters based on those changes in an adaptive manner using a wearable device. The monitoring is not limited to a fixed view point, but rather, may be used to facilitate driver and passenger comfort alike.

In one embodiment, the wearable device is configured to identify the user based on the sensed one or more physiological parameters, wherein the adjustment of the one or more vehicle parameters is based on pre-defined user settings. A user, whether driver or passenger, once identified by the wearable device, causes adjustment in pre-defined settings for that user (e.g., as learned) including one or any combination of vehicle seat settings, mirror settings, interior climate settings, playback of one or a combination of video or audio playback, driving plan settings, or game console settings.

In one embodiment, the wearable device is further configured to: receive a changed value for at least one of the one or more physiological parameters; and cause adjustment of the one or more vehicle parameters based on the changed value, the adjustment altering at least one of the pre-defined user settings. For instance, should a user recently experience lower back trauma, as monitored by postural information acquired even outside of the vehicle by accelerometer sensors in the wearable device, upon identification, adjustments may be caused by signaling of the wearable device to vehicle logic resulting in a change to the pre-defined user settings (e.g., the lumbar control of the seat may be activated to a new position that alleviates pain, or the seat may be moved closer than the pre-defined setting to reduce stress on the lower back).

In one embodiment, the one or more vehicle parameters are associated with passenger-focused settings or driver-focused settings. As indicated above, given the mobility inherent in a wearable device, there is no constraint on whom in the vehicle is the subject of monitoring.

In one embodiment, wherein the one or more physiological parameters comprise patterns in heart rate, heart rate variability, electrodermal activity, voice, facial features, fingerprint features, iris features, tongue features, ear features, respiration, activity, or sleep signals. The use of the wearable device enables one or a host of physiological parameters to be monitored, enabling refinement in the vehicle settings that are optimal for the user.

In one embodiment, the wearable device is further configured to interpret the one or more physiological parameters as an indication that the user's ability to operate a vehicle is compromised, and wherein the causing of the adjustment of the one or more vehicle parameters comprises preventing the vehicle from starting. For instance, the wearable device can measure blood alcohol levels in a driver, and if those levels exceed the legal limit (or some other threshold), the wearable device can cause the vehicle to be disabled.

In one embodiment, the wearable device is configured to, prior to receiving and causing, receive a first set of physiological parameters; monitor changes to the one or more vehicle parameters; and correlate the changes to the one or more vehicle parameters to the first set of physiological parameters. For instance, the wearable device learns of the user's preference settings by receiving (e.g., from the vehicle logic) feedback of setting adjustments made by the user and correlates those settings to the sensed physiological parameters, such that the next time the user in in the vehicle, the physiological parameters detected by the wearable device are used to choose those settings. In some embodiments, the learning may be implemented at another device or devices (e.g., in the cloud or a central computing device), with the learned output communicated to the wearable device.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Disclosed herein are certain embodiments of a vehicle settings adjustment system that identify a user (e.g., driver or passenger) and/or physiological state based on their health/physiological data measured via a wearable device and automatically adjust one or more vehicle parameters (e.g., vehicle settings) corresponding to personal preferences of the identified user. Additionally, the wearable device may operate as a replacement to a personal key, enabling access and/or control of the vehicle. In one embodiment, the wearable device is worn around the wrist of the user, and comprises one or more sensors that measure one or more physiological parameters of the user. The wearable device further comprises one or more processors that receive the one or more physiological parameters and cause adjustment of one or more vehicle parameters based on the received one or more physiological parameters. In one embodiment, the wearable device causes the adjustment by communicating a signal to vehicle logic, which triggers the vehicle logic to adjust a vehicle parameter or parameters based on the physiological parameter. The signal may be sent wirelessly (e.g., via Bluetooth), and includes an identity of the user (based on identification using the sensed physiological parameter(s) at the wearable device) that the vehicle logic uses to match with stored pre-defined settings (e.g., personal preferences) of the user. In some embodiments, the signal may include sensed physiological parameters that are interpreted by the vehicle logic as requiring a change in vehicle parameter(s) adjustment without identifying the user. For instance, the physiological parameter may indicate a lower skin temperature of the user (e.g., the user is cold), and hence the wearable device may signal the vehicle logic to adjust a seat heater setting and/or interior environment control to increase the temperature (to warm the user), regardless of the identity of the user (though in some embodiments, the vehicle logic may both identify the user and make an adjustment adapting to the changed physiological parameter for which the personal preferences are set). In some embodiments, the signal communicated by the wearable device to the vehicle logic may include both the identity and the physiological parameters, the former enabling a match by the vehicle logic of the appropriate pre-defined settings and the latter altering any of the settings to adapt to the current physiological measurements for that user. In some embodiments, the physiological parameters may be communicated to the vehicle logic, and recognition software may be embedded in the vehicle logic instead of at the wearable device to identify the user based on those communicated physiological parameters.

Digressing briefly, conventional systems either use a personalized key to make adjustments or, as taught by the Lemelson reference, use fixed imaging and fingerprinting systems to identify the driver to enable the access to and implementation of stored personal settings within the vehicle. In contrast, certain embodiments of a vehicle settings adjustment system operate using wearable devices, which are conveniently worn by the user in and outside of the vehicle to collect even more information about the user to trigger adjustments in vehicle parameter(s) that are adaptive to current user conditions (driver and passenger) while also improving comfort and even safety of the user when inside the vehicle. Further, the wearable device enables a replacement of the key for enabling access to, and control of, the vehicle without the inconvenience or distraction of scanning accessories within the vehicle, which may be damaged or for which signals may be obstructed or altered due to contact by individuals and/or items within the vehicle.

Having summarized certain features of a vehicle settings adjustment system of the present disclosure, reference will now be made in detail to the description of a vehicle settings adjustment system as illustrated in the drawings. While a vehicle settings adjustment system will be described in connection with these drawings, there is no intent to limit the vehicle settings adjustment system to the embodiments disclosed herein. For instance, though described primarily in the context of communications between a wearable device comprising one or more sensors and vehicle logic (also referred to herein as a vehicle processing unit), in some embodiments, communications may include other or alternative components/devices, including a remote server(s), such as found in a cloud platform, and/or a mobile device of the user. As another example, the sensors of the wearable device are described herein as a source of measurement of the one or more physiological parameters of the user(s), though in some embodiments, the vehicle logic may use other and/or additional sources of measurement, including internal sensors located in the interior of the vehicle, mobile device sensors, and/or external vehicle sensors in some embodiments. Further, though described in the context of a human driver and zero or more passengers, it should be appreciated that in some embodiments, the vehicle settings adjustment system may be used with autonomous driving machines, where automatic adjustments to the vehicle parameters to accommodate only a passenger or passengers may be implemented, such as via the detection of parameters and matching to either user-settings in a remote data storage, or without access to preferences and merely using the physiological measures to trigger adjustments to the one or more vehicle parameters. Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents consistent with the disclosure as defined by the appended claims. Further, it should be appreciated in the context of the present disclosure that the claims are not necessarily limited to the particular embodiments set out in the description.

Figure 1:
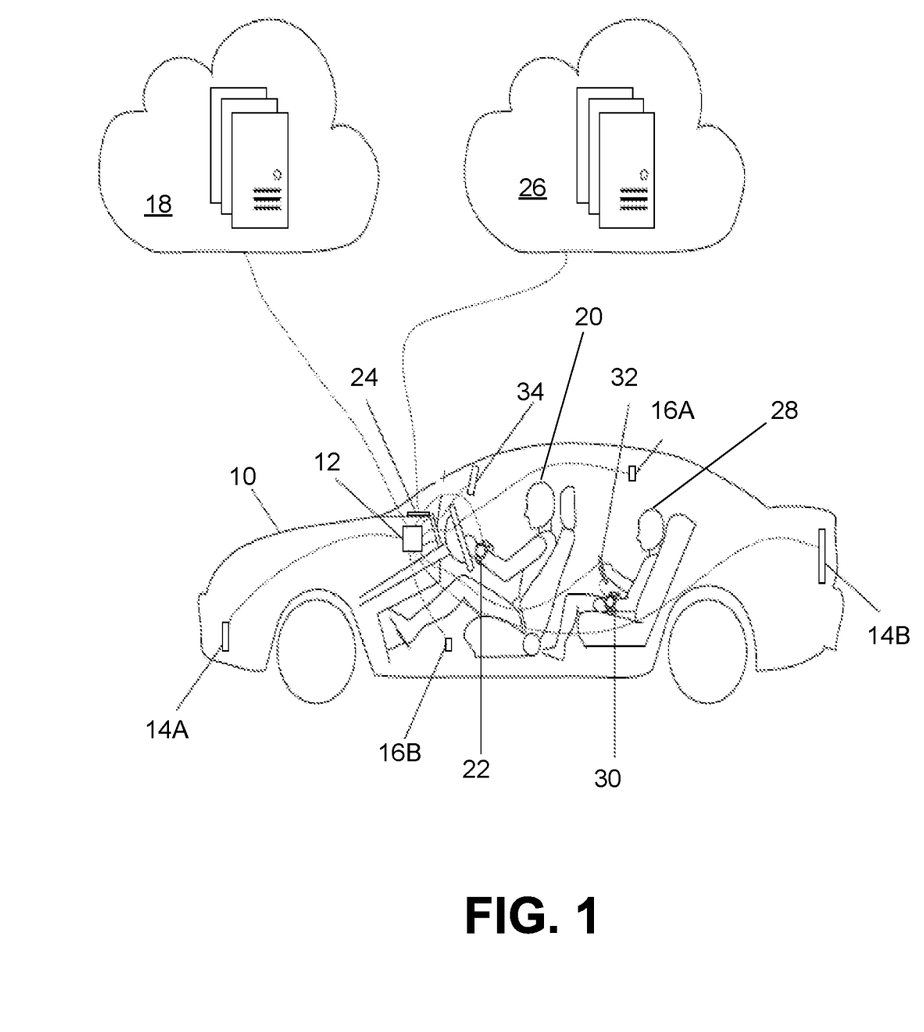
FIG. 1 is a schematic diagram that illustrates an example vehicle in which a vehicle settings adjustment system is used, in accordance with an embodiment of the invention.

Referring now to FIG. 1, shown is an example vehicle 10 in which certain embodiments of a vehicle settings adjustment system may be implemented. It should be appreciated by one having ordinary skill in the art in the context of the present disclosure that the vehicle 10 is one example among many, and that some embodiments of a vehicle settings adjustment system may be used in other types of vehicles than the type depicted in FIG. 1. FIG. 1 illustrates the vehicle 10 having a vehicle processing unit 12, external vehicle sensors 14 (e.g., front 14A and rear 14B sensors), and internal vehicle sensors 16 (e.g., 16A and 16B). Note that the quantity of sensors 14, 16 and vehicle processing unit 12 is illustrative of one embodiment, and that in some embodiments, fewer or greater quantities of one or more of these types of components may be used. The internal vehicle sensors 16 are located in the cabin of the vehicle 10. The external vehicle sensors 14 are located on the exterior of the vehicle 10. The external vehicle sensors 14 and internal vehicle sensors 16 are capable of communicating with the vehicle processing unit 12, such as via a wireless medium (e.g., Bluetooth, near field communications (NFC), wireless fidelity (e.g., Wi-Fi), and/or one of various known light-coding technologies, among others, and/or wired medium (e.g., over a CAN bus or busses). The internal vehicle sensors 16 may include at least one of temperature sensors, microphones, cameras, light sensors, pressure sensors, accelerometers, proximity sensors, including beacons, radio frequency identification (RFID) or other coded light technologies, among other sensors. The external vehicle sensors 14 may include at least one of temperature sensors, sensors to measures precipitation and/or humidity, microphones, cameras, light sensors, pressure sensors, accelerometers, etc. In some embodiments, the vehicle 10 includes a geographic location sensor (e.g., a Global Navigation Satellite Systems (GNSS) receiver, including Global Position Systems (GPS) receiver, among others). The geographic location sensor provides location coordinates (e.g., latitude, longitude, altitude). The vehicle 10 also includes vehicle sensors related to the operation of the vehicle 10 (e.g., speed, braking, turning of the steering wheel, turning of the wheels, etc.).

FIG. 1 further illustrates the vehicle processing unit 12 capable of communicating with at least one cloud (e.g., cloud 1) 18. That is, the vehicle processing unit 12 is capable of communicating (e.g., via telemetry, such as according to one or more networks configured according to, say, the Global System for Mobile Communications or GSM standard, among others) with one or more devices of the cloud platform (the cloud 18). In one embodiment, pre-defined user settings, also referred to as user preferences (e.g., for the driver and/or passengers), for vehicle parameters (vehicles settings) may be stored on a device or devices of the cloud 18. For instance, upon the vehicle processing unit 12 receiving the physiological parameter(s) for, and/or an identity of, an occupant of the vehicle, the vehicle processing unit 12 may access the stored settings using the identified occupant as an index, and use these user settings to make adjustments to the vehicle parameters according to those settings (or as modified by any changes in the physiological parameters from default user settings).

The vehicle 10 is capable of being driven by a (human) driver 20 that primarily controls navigation (e.g., direction, vehicle speed, acceleration, etc.) of the vehicle 10. In some embodiments, the vehicle 10 may operate autonomously (without a human driver). The driver 20 may drive the vehicle 10 while wearing a wearable 22 (herein, also referred to as the driver wearable or wearable device). The driver wearable 22 may include, for example, a Philips Health Watch or another fitness tracker or smartwatch. In some embodiments, the driver wearable 22 may include a chest strap, arm band, ear piece, necklace, belt, clothing, headband, or another type of wearable form factor comprising one or more physiological sensors. In some embodiments, the driver wearable 22 may be an implantable device, which may include biocompatible sensors that reside underneath the skin or are implanted elsewhere. The driver 20 may also wear the driver wearable 22 when he is not driving the vehicle 10. The driver 20 may further drive the vehicle 10 while in possession of his driver mobile device 24 (e.g., smart phone, tablet, laptop, notebook, computer, etc.) present in the vehicle 10. The driver wearable 22 is capable of communicating (e.g., via Bluetooth, 802.11, NFC, etc.) with the driver mobile device 24 and mobile software applications ("apps") residing thereon and/or the vehicle processing unit 12. The driver mobile device 24 is capable of communicating with at least one cloud (e.g., cloud 2) 26. In some cases, the driver mobile device 24 is capable of communicating with the vehicle processing unit 12.

At times, a passenger 28 may ride in the vehicle 10 with the driver 20. In some cases, the passenger 28 may wear a wearable 30 (also referred to herein as a passenger wearable or wearable device). In some cases, a passenger mobile device 32 (e.g., smart phone, tablet, laptop, notebook, computer, etc.) may be present with the passenger 28 in the vehicle 10. The passenger wearable 30 is capable of communicating with the passenger mobile device 32. The passenger mobile device 32 is capable of communicating with at least one cloud (e.g., cloud 2) 26. In some embodiments, the passenger mobile device 32 is capable of communicating with the vehicle processing unit 12. Further discussion of the mobile devices 24 and 32 are described below. Other examples of mobile devices 24 and 32 may be found in International Application Publication No. WO2015084353A1, filed Dec. 4, 2013, entitled "Presentation of physiological data," which describes an example of a user device embodied as a driver mobile device and a passenger mobile device.

In general, the wearable devices 22, 30 may be in wireless communications with the vehicle processing unit 12 and with respective mobile devices 24, 32. In some embodiments, the wearable devices 22, 30 may be in communication with one or both clouds 18, 26, either directly (e.g., via telemetry, such as through a cellular network) or via an intermediate device (e.g., mobile devices 24, 32, respectively). Similarly, the vehicle processing unit 12 may be in communication with one or both clouds 18, 26. In some embodiments, all devices within the vehicle 10 may be in communication with one another and/or with the cloud(s) 18, 26.

The network enabling communications to device(s) in the clouds 18, 26 may include any of a number of different digital cellular technologies suitable for use in the wireless network, including: GSM, GPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others. In some embodiments, communications with devices in the clouds 18, 26 may be achieved using Wi-Fi. Access to the clouds 18, 26, which may be part of a wide area network that comprises one or a plurality of networks that in whole or in part comprise the Internet, may be further enabled through access to one or more networks including PSTN (Public Switched Telephone Networks), POTS, Integrated Services Digital Network (ISDN), Ethernet, Fiber, DSL/ADSL, Wi-Fi, Zigbee, BT, BTLE, among others.

Clouds 18, 26 may each comprise an internal cloud, an external cloud, a private cloud, or a public cloud (e.g., commercial cloud). For instance, a private cloud may be implemented using a variety of cloud systems including, for example, Eucalyptus Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, services of the clouds 18, 26 may be implemented in some embodiments according to multiple, logically-grouped servers (run on server devices), referred to as a server farm. The devices of the server farm may be geographically dispersed, administered as a single entity, or distributed among a plurality of server farms, executing one or more applications on behalf of or in conjunction with one or more of the wearables 22, 30, the mobile devices 24, 32, and/or the vehicle processing unit 12. The devices within each server farm may be heterogeneous. One or more of the devices of the server farm may operate according to one type of operating system platform (e.g., WINDOWS NT, manufactured by Microsoft Corp. of Redmond, Wash.), while one or more of the other devices may operate according to another type of operating system platform (e.g., Unix or Linux). The group of devices of the server farm may be logically grouped as a farm that may be interconnected using a wide-area network (WAN) connection or medium-area network (MAN) connection, and each device may each be referred to as (and operate according to) a file server device, application server device, web server device, proxy server device, or gateway server device.

In some embodiments, the vehicle 10 also includes at least one camera 34. The camera 34 may be located to view the driver's face. In some embodiments, the camera 34 is located to view the passenger's face. In some embodiments, the vehicle 10 may include multiple cameras for viewing the people in the vehicle 10. The camera 34 is capable of communicating with at least one of the vehicle processing unit 12, the wearables 22, 30, the mobile devices 24, 32, and/or the cloud (e.g., cloud 18 and/or cloud 26). In some embodiments, the camera 34 includes a vital signs camera, such as the Philips Vital Signs Camera. The Vital Signs Camera remotely measures heart and breathing rate using a standard, infrared (IR) based camera by sensing changes in skin color and body movement (e.g., chest movement). For instance, whenever the heart beats, the skin color changes because of the extra blood running through the vessels. Algorithms residing within the Vital Signs Camera detect these tiny skin color changes, amplify the signals, and calculate a pulse rate signal by analyzing the frequency of the color changes. For respiration, the Vital Signs Camera focuses on the rise and fall of the chest and/or abdomen, amplifying the signals using algorithms and determining an accurate breathing rate. The Vital Signs Camera is also motion robust, using facial tracking to obtain an accurate reading during motion. The Vital Signs Camera, with its unobtrusive pulse and breathing rate capabilities, enables tracking of moods, sleep patterns, and activity levels, and can be used to help detect driver and/or passenger drowsiness (e.g., sleepiness levels), stress, and attention levels. In general, pulse and breathing rate monitoring are useful when monitoring health, particularly as physiological indicators of emotion. Note that camera functionality in the wearable devices 22, 30 and/or mobile devices 24, 32 may have the same or similar functionality in some embodiments.

The driver wearable 22 and/or passenger wearable 30 includes at least one of an accelerometer, photoplethysmogrpm (PPG) sensor, sensors for detecting electrodermal activity (EDA) (e.g., detects a variation in the electrical characteristics of the skin, including skin conductance, galvanic skin response, electrodermal response), blood pressure cuff, blood glucose monitor, electrocardiogram sensor, step counter sensor, gyroscope, Sp02 sensor (e.g., providing an estimate of arterial oxygen saturation), respiration sensor, posture sensor, stress sensor, galvanic skin response sensor, temperature sensor, pressure sensor, light sensor, camera sensor (e.g., with the same or similar functionality of the camera 34, including facial and/or iris recognition capabilities), fingerprint reader (e.g., solid state, optical), ear and/or tongue sense-functionality, voice recognition sensors, and/or other physiological parameter sensors. The driver wearable 22 and/or passenger wearable 30 are capable of sensing signals related to heart rate, heart rate variability, respiration rate, pulse transit time, blood pressure, temperature, among other physiological parameters. Other possible parameters and sensors are described in Table 1 of U.S. Pat. No. 8,398,546, filed Sep. 13, 2004, and entitled "System for monitoring and managing body weight and other physiological conditions including iterative and personalized planning, intervention and reporting capability." In some embodiments, the sensors described above for the driver wearable 22 may be integrated in structures of the vehicle 10 instead (e.g., not worn by the driver 20), yet positioned proximate to the driver 20 in the vehicle 10. For example, the vehicle steering wheel may include one of the sensors (e.g., an ECG sensor). As another example, the driver's seat of the vehicle 10 may include a sensor (e.g., a pressure sensor).

Processing for certain embodiments of the vehicle settings adjustment system may be included in one or any combination of the vehicle processing unit 12, a cloud (e.g., one or more devices of the clouds 18 and/or 26), the driver wearable 22, the passenger wearable 30, the driver mobile device 24, the passenger mobile device 32, and/or the camera 34. For instance, user identification and/or user preferences (e.g., for vehicle parameter adjustments) may be achieved and/or stored, respectively, at any one or more of these devices based on sensed physiological parameters. Further, sensing of physiological parameters may be achieved via the mobile devices 24, 32, interior and exterior sensors 16, 14, respectively, camera 34, and/or the one or more sensors of the wearable devices 22, 30. However, in the interest of facilitating an understanding of operation of certain embodiments of a vehicle settings adjustment system and further in the interest of brevity, the description that follows focuses on the measurement of physiological parameters and any identification of the user using one or more sensors of the wearable devices 22 and/or 30, and determination of vehicle parameters (whether via access to pre-defined settings locally or remotely stored and/or without using an identity of the user) is described as being performed by the vehicle processing unit 12, with the understanding that variations to the described embodiments where these functions are implemented elsewhere among the various devices depicted in FIG. 1 are also contemplated and hence within the scope of the invention.

Figure 2:
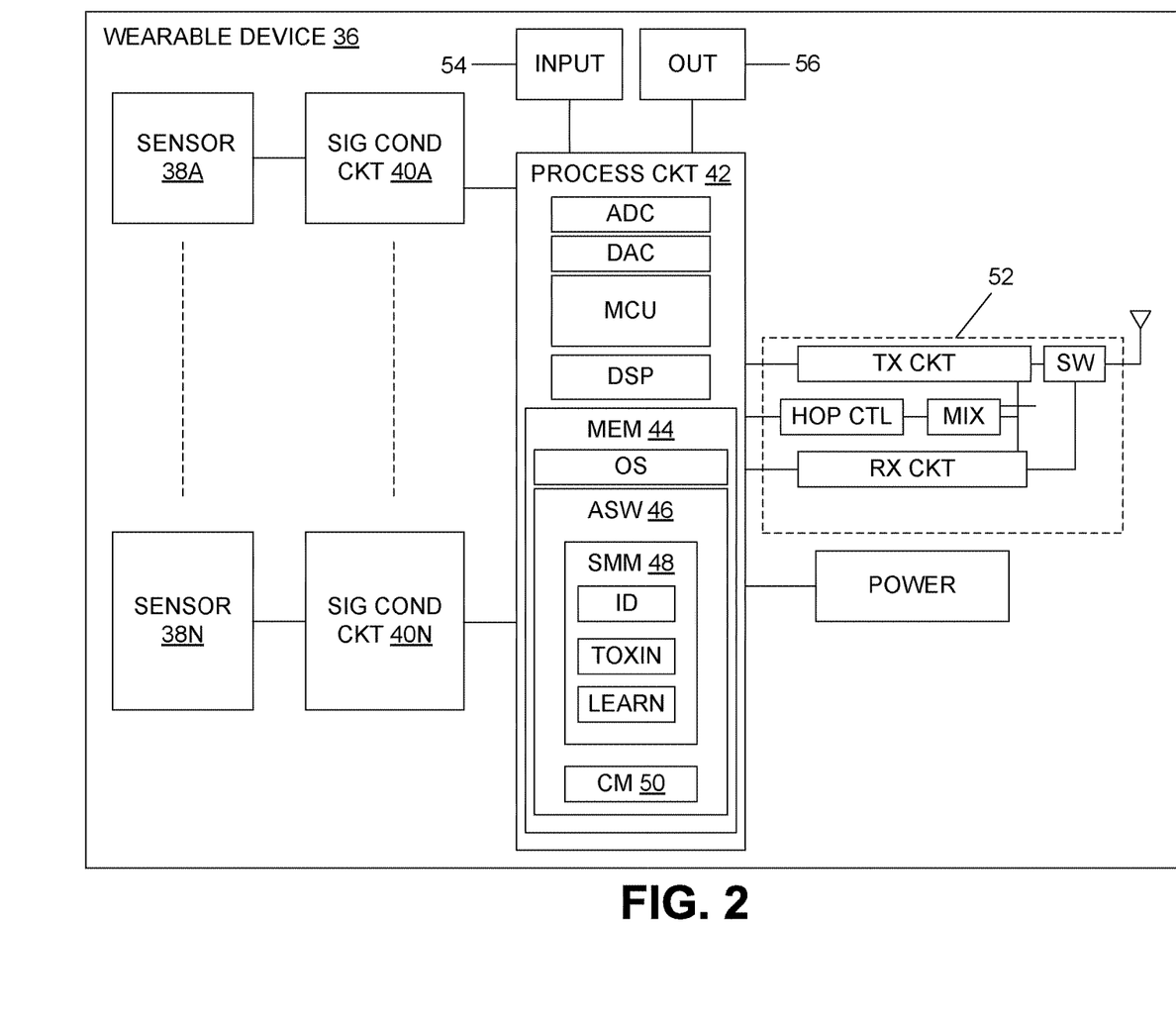
FIG. 2 is a schematic diagram that illustrates an example wearable device in which all or a portion of the functionality of a vehicle settings adjustment system may be implemented, in accordance with an embodiment of the invention.

Attention is now directed to FIG. 2, which illustrates an example wearable device 36 in which all or a portion of the functionality of a vehicle settings adjustment system may be implemented. The driver wearable 22 or the passenger wearable 30 may be constructed according to the architecture and functionality of the wearable device 36 depicted in FIG. 2. In particular, FIG. 2 illustrates an example architecture (e.g., hardware and software) for the example wearable device 36. It should be appreciated by one having ordinary skill in the art in the context of the present disclosure that the architecture of the wearable device 36 depicted in FIG. 2 is but one example, and that in some embodiments, additional, fewer, and/or different components may be used to achieve similar and/or additional functionality. In one embodiment, the wearable device 36 comprises one, or as shown, a plurality of sensors 38 (e.g., 38A-38N), one or more signal conditioning circuits 40 (e.g., SIG COND CKT 40A-SIG COND CKT 40N) coupled respectively to the sensors 38, and a processing circuit 42 (comprising one or more processors) that receives the conditioned signals from the signal conditioning circuits 40. In one embodiment, the processing circuit 42 comprises an analog-to-digital converter (ADC), a digital-to-analog converter (DAC), a microcontroller unit (MCU), a digital signal processor (DSP), and memory (MEM) 44. In some embodiments, the processing circuit 42 may comprise fewer or additional components than those depicted in FIG. 2. For instance, in one embodiment, the processing circuit 42 may consist entirely of the microcontroller unit. In some embodiments, the processing circuit 42 may include the signal conditioning circuits 40.

The memory 44 comprises an operating system (OS) and application software (ASW) 46, which in one embodiment comprises one or more functionality of a vehicle settings adjustment system. In some embodiments, additional software may be included for enabling physical and/or behavioral tracking, among other functions. In the depicted embodiment, the application software 46 comprises a sensor measurement module (SMM) 48 for processing signals received from the sensors 38 and a communications module (CM) 50 for communicating the measured physiological parameters (e.g., raw or derived).

As used herein, the term "module" may be understood to refer to computer executable software, firmware, hardware, and/or various combinations thereof. It is noted there where a module is a software and/or firmware module, the module is configured to affect the hardware elements of an associated system. It is further noted that the modules shown and described herein are intended as examples. The modules may be combined, integrated, separated, or duplicated to support various applications. Also, a function described herein as being performed at a particular module may be performed at one or more other modules and by one or more other devices instead of or in addition to the function performed at the particular module. Further, the modules may be implemented across multiple devices or other components local or remote to one another. Additionally, the modules may be moved from one device and added to another device, or may be included in both devices.

The sensor measurement module 48 comprises executable code (instructions) to process the signals (and associated data) measured by the sensors 38. For instance, the sensors 38 may measure one or more (physiological) parameters including heart rate, heart rate variability, electrodermal activity, body motion (e.g., using single or tri-axial accelerometer measurements), voice patterns, facial features, iris features/patterns, fingerprint features/patterns, tongue and/or ear features/patterns, respiration, activity, sleep signals, among others. One or more of these parameters may be analyzed by the sensor measurement module 48. In some embodiments, raw data and/or derived data corresponding to one or more of the parameters is communicated to the vehicle processing unit 12 (FIG. 1), which analyzes the parameters and identifies the user and/or determines vehicle parameters to adjust based on these parameters. In some embodiments, one or more functionality of the sensor measurement module 48 may be achieved at additional or alternate devices (e.g., the mobile device(s) 24, 32, camera 34, and/or external and/or internal sensors 14, 16 (FIG. 1)). The sensor measurement module 48 may control the sampling rate of one or more of the sensors 38. In one embodiment, the sensor measurement module 48 further comprises an identification (ID) module, which enables an identification of the user based on the physiological signals. For instance, the identification module in conjunction with the sensors 38 provides for iris scanning functionality, voice recognition, tongue scanning, ear scanning, and/or fingerprint reading. Such scanning is looking to identify unique patterns associated with a respective user. In some embodiments, a single scan of a feature (e.g., iris scanning) may be used for identification, and in some embodiments, a combination of two or more of these techniques may be used. Note that in some embodiments, functionality pertaining to the identification module may be present in the vehicle processing unit 12 (FIG. 1) instead, wherein the wearable device 36 communicates the physiological parameters and the vehicle processing unit 12 uses the received data to identify the user. In some embodiments, the identification module may be located in another and/or additional device, such as in the cloud(s) 18, 26. As explained above, in some embodiments, an identification module may be omitted. The sensor measurement module 48 further comprises a toxins (TOXIN) module, which in conjunction with the sensors 38, enables a determination of whether or not the user is incapable of safely driving the vehicle 10 based on an indication of an incapacitating or near incapacitating amount of toxin (e.g., alcohol, opioids, etc.) in his or her system. For instance, the toxins module may receive sensor data indicating excessive alcohol in the blood (e.g., higher heart rate, higher skin conductivity, skin color changes, etc.), and signal to the vehicle processing unit 12, which in turn may either prevent access to the vehicle 10 or disable the vehicle 10, preventing the user from getting behind the wheel and causing a risk of harm to others and/or himself/herself. The sensor measurement module 48 may also include a learning (LEARN) module, though in some embodiments, the learning module may be located also, or alternatively, at one or more other devices, including the vehicle processing unit 12, the cloud(s) 18, 26, etc. The learning module is used in conjunction with sensor data to learn about patterns in behavior of the user, including determining user preferences for vehicle parameters. For instance, the learning module may correlate sensed physiological parameters with actions taken by the user that result in adjustments in one or more vehicle parameters. The actions taken by the user may be sensed by sensors 38 of the wearable device 36, such as sensing movement/adjustment of the seat of the vehicle 10 via proximity sensors, inertial sensors, and/or pressure sensors in the wearable device 36, sensing audio volume via a microphone in the wearable device 36, internal temperature via temperature sensors, etc. In some embodiments, adjustments initiated by the user may be communicated by the vehicle processing unit 12 to the wearable device 36. Based on the learning module using, for instance, a stimuli/response correlation that is proximal in time, the wearable device 36 may associate certain physiological parameters and/or the identity of the user with these changes and store as user preferences. The user preferences may then be communicated to the vehicle processing unit 12 for storage therein (or in some embodiments, communicated to the cloud(s) 18, 26 (FIG. 1)). The stored preferences may be accessed at a later time of entry, by the user, into the vehicle 10, which upon sensing the physiological parameters, the wearable device 36 communicates these parameters to the vehicle processing unit 12. The vehicle processing unit 12 may look for a match to the stored user preferences, and cause adjustment to the vehicle parameters according to these preferences (or as further adjusted based on a changed value of the one or more physiological parameters) based on a match. The learning module may include one or any variety of known machine learning algorithms, including random forest, regression models, (deep) neural networks, among others. In some embodiments, additional modules used to achieve the disclosed functionality of a vehicle settings adjustment system, among other functionality, may be included, or one or more of the modules 48-50 may be separate from the application software 46 or packaged in a different arrangement than shown relative to each other. In some embodiments, fewer than all of the modules 48-50 may be used in the wearable device 36.

The communications module 50 comprises executable code (instructions) to enable a communications circuit 52 of the wearable device 36 to operate according to one or more of a plurality of different communication technologies (e.g., NFC, Bluetooth, Zigbee, 802.11, Wi-Fi, GSM, etc.) to receive data from, and/or transmit data to, one or more devices (e.g., other wearable devices, mobile devices, cloud devices, vehicle processing unit, cameras, etc.) internal to the vehicle 10 or external to the vehicle 10. For purposes of illustration, the communications module 50 in conjunction with the communications circuit 52 is described hereinafter primarily as communicating signals to the vehicle processing unit 12 (FIG. 1), which in turn causes adjustment to one or more vehicle parameters as explained below. As described earlier, those signals may include one or any combination of one or more physiological parameters or an identification of the user. In one embodiment, one or more sensed parameters and/or identification are communicated to the vehicle processing unit 12 via the communications circuit 52 in conjunction with the communications module 50. As explained above, the parameters and/or identity are analyzed by the vehicle processing unit 12, which in turn causes an adjustment to be effected in one or more vehicle parameters.

As indicated above, in one embodiment, the processing circuit 42 is coupled to the communications circuit 52. The communications circuit 52 serves to enable wireless communications between the wearable device 36 and other devices within or external to the vehicle 10 (FIG. 1). The communications circuit 52 is depicted as a Bluetooth (BT) circuit, though not limited to this particular transceiver configuration. For instance, in some embodiments, the communications circuit 52 may be embodied as any one or a combination of an NFC circuit, Wi-Fi circuit, transceiver circuitry based on Zigbee, BT low energy, 802.11, GSM, LTE, CDMA, WCDMA, among others such as optical or ultrasonic based technologies. In some embodiments, plural transceiver circuits according to more than one of the communication specifications/standards described above may be used.

The processing circuit 42 is further coupled to input/output (I/O) devices or peripherals, including an input interface 54 (INPUT) and an output interface 56 (OUT). In some embodiments, an input interface 54 and/or output interface 56 may be omitted, or functionality of both may be combined into a single component (e.g., touch-type display screen).

Note that in some embodiments, functionality for one or more of the aforementioned circuits and/or software may be combined into fewer components/modules, or in some embodiments, further distributed among additional components/modules or devices. For instance, the processing circuit 42 may be packaged as an integrated circuit that includes the microcontroller (microcontroller unit or MCU), the DSP, and memory 44, whereas the ADC and DAC may be packaged as a separate integrated circuit coupled to the processing circuit 42. In some embodiments, one or more of the functionality for the above-listed components may be combined, such as functionality of the DSP performed by the microcontroller.

As indicated above, the sensors 38 comprise one or any combination of sensors capable of measuring physiological parameters. For instance, typical physiological parameters include heart rate, heart rate variability, heart rate recovery, blood flow rate, activity level, muscle activity (including core movement, body orientation/position, power, speed, acceleration, etc.), muscle tension, blood volume, blood pressure, blood oxygen saturation, respiratory rate, perspiration, skin temperature, electrodermal activity (skin conductance response, galvanic skin response, electrodermal response, etc.), body weight, body composition (e.g., body mass index or BMI), articulator movements (especially during speech), iris scans (e.g., using imaging sensors), fingerprint scans (e.g., using a semiconductive or optical reader), ear and/or tongue scans, and voice pattern measurement (e.g., using a microphone). The physiological parameters may be used to determine various information. Note that in some embodiments, the data from the sensors 38 may be supplemented by vehicle sensors (e.g., sensors 14, 16, camera 34) and/or mobile device sensors, and in some embodiments, sensor data from the vehicle sensors and/or mobile device sensors may be used in place of the wearable sensor(s). In some embodiments, as indicated above, the sensors 38 may include GNSS sensors, including a GPS receiver to facilitate determinations of distance, speed, acceleration, location, altitude, etc. (e.g., location data, or generally, sensing movement). In some embodiments, GNSS sensors (e.g., GNSS receiver and antenna(s)) may be included in the mobile device(s) 24, 32 (FIG. 1) and/or the vehicle 10 (FIG. 1), in addition to, or in lieu of, those residing in the wearable device 36. In some embodiments, GNSS functionality may be achieved via the communications circuit 52 or other circuits coupled to the processing circuit 42. Other information (e.g., contextual) includes historical data on behavioral or activity patterns of the user. For instance, location data may be used in some embodiments in conjunction with services accessed via the Internet, including mapping services that are accessed from the Internet (e.g., using browser functionality) or other remote devices (e.g., using virtual private networks, application programming interfaces, etc.). Other and/or additional data includes social media, and/or calendar data to obtain contextual data (e.g., with the location data) to enable learning (e.g., by the learning module) of user activity patterns behavior. In some embodiments, one or more of the services may be located in memory of the vehicle processing unit or other vehicle memory. The sensors 38 may also include flex and/or force sensors (e.g., using variable resistance), electromyographic sensors, electrocardiographic sensors (e.g., EKG, ECG), magnetic sensors, photoplethysmographic (PPG) sensors, bio-impedance sensors, infrared proximity sensors, acoustic/ultrasonic/audio sensors, a strain gauge, galvanic skin/sweat sensors, pH sensors, temperature sensors, and photocells. The sensors 38 may include other and/or additional types of sensors for the detection of environmental parameters and/or conditions, for instance, barometric pressure, humidity, outdoor temperature, pollution, noise level, etc. One or more of these sensed environmental parameters/conditions may be used (e.g., by the vehicle processing unit 12) in the determination of proper vehicle parameter adjustment (e.g., to automatically turn on the vehicle 10 and change the interior temperature of the vehicle 10, such as before the user has entered the vehicle 10 from the house or other establishment on a cold weather day). Note that one or more of the sensors 38 may be constructed based on piezoelectric, piezoresistive or capacitive technology in a microelectromechanical system (MEMS) infrastructure.

The signal conditioning circuits 40 include amplifiers and filters, among other signal conditioning components, to condition the sensed signals including data corresponding to the sensed physiological parameters and/or location signals before further processing is implemented at the processing circuit 42. Though depicted in FIG. 2 as respectively associated with each sensor 38, in some embodiments, fewer signal conditioning circuits 40 may be used (e.g., shared for more than one sensor 38). In some embodiments, the signal conditioning circuits 40 (or functionality thereof) may be incorporated elsewhere, such as in the circuitry of the respective sensors 38 or in the processing circuit 42 (or in components residing therein). Further, although described above as involving unidirectional signal flow (e.g., from the sensor 38 to the signal conditioning circuit 40), in some embodiments, signal flow may be bi-directional. For instance, in the case of optical measurements, the microcontroller may cause an optical signal to be emitted from a light source (e.g., light emitting diode(s) or LED(s)) in or coupled to the circuitry of the sensor 38, with the sensor 38 (e.g., photocell) receiving the reflected/refracted signals.

The communications circuit 52 is managed and controlled by the processing circuit 42 (e.g., executing the communications module 50). The communications circuit 52 is used to wirelessly interface with the vehicle processing unit 12 (FIG. 1) and/or in some embodiments, one or more devices within and/or external to the vehicle 10 (FIG. 1). In one embodiment, the communications circuit 52 may be configured as a Bluetooth transceiver, though in some embodiments, other and/or additional technologies may be used, such as Wi-Fi, GSM, LTE, CDMA and its derivatives, Zigbee, NFC, among others. In the embodiment depicted in FIG. 2, the communications circuit 52 comprises a transmitter circuit (TX CKT), a switch (SW), an antenna, a receiver circuit (RX CKT), a mixing circuit (MIX), and a frequency hopping controller (HOP CTL). The transmitter circuit and the receiver circuit comprise components suitable for providing respective transmission and reception of an RF signal, including a modulator/demodulator, filters, and amplifiers. In some embodiments, demodulation/modulation and/or filtering may be performed in part or in whole by the DSP. The switch switches between receiving and transmitting modes. The mixing circuit may be embodied as a frequency synthesizer and frequency mixers, as controlled by the processing circuit 42. The frequency hopping controller controls the hopping frequency of a transmitted signal based on feedback from a modulator of the transmitter circuit. In some embodiments, functionality for the frequency hopping controller may be implemented by the microcontroller or DSP. Control for the communications circuit 52 may be implemented by the microcontroller, the DSP, or a combination of both. In some embodiments, the communications circuit 52 may have its own dedicated controller that is supervised and/or managed by the microcontroller.

In one example operation for the communications circuit 52, a signal (e.g., at 2.4 GHz) may be received at the antenna and directed by the switch to the receiver circuit. The receiver circuit, in cooperation with the mixing circuit, converts the received signal into an intermediate frequency (IF) signal under frequency hopping control attributed by the frequency hopping controller and then to baseband for further processing by the ADC. On the transmitting side, the baseband signal (e.g., from the DAC of the processing circuit 42) is converted to an IF signal and then RF by the transmitter circuit operating in cooperation with the mixing circuit, with the RF signal passed through the switch and emitted from the antenna under frequency hopping control provided by the frequency hopping controller. The modulator and demodulator of the transmitter and receiver circuits may perform frequency shift keying (FSK) type modulation/demodulation, though not limited to this type of modulation/demodulation, which enables the conversion between IF and baseband. In some embodiments, demodulation/modulation and/or filtering may be performed in part or in whole by the DSP. The memory 44 stores the communications module 50, which when executed by the microcontroller, controls the Bluetooth (and/or other protocols) transmission/reception.

Though the communications circuit 52 is depicted as an IF-type transceiver, in some embodiments, a direct conversion architecture may be implemented. As noted above, the communications circuit 52 may be embodied according to other and/or additional transceiver technologies.

The processing circuit 42 is depicted in FIG. 2 as including the ADC and DAC. For sensing functionality, the ADC converts the conditioned signal from the signal conditioning circuit 40 and digitizes the signal for further processing by the microcontroller and/or DSP. The ADC may also be used to convert analogs inputs that are received via the input interface 54 to a digital format for further processing by the microcontroller. The ADC may also be used in baseband processing of signals received via the communications circuit 52. The DAC converts digital information to analog information. Its role for sensing functionality may be to control the emission of signals, such as optical signals or acoustic signals, from the sensors 38. The DAC may further be used to cause the output of analog signals from the output interface 56. Also, the DAC may be used to convert the digital information and/or instructions from the microcontroller and/or DSP to analog signals that are fed to the transmitter circuit. In some embodiments, additional conversion circuits may be used.

The microcontroller and the DSP provide processing functionality for the wearable device 36. In some embodiments, functionality of both processors may be combined into a single processor, or further distributed among additional processors. The DSP provides for specialized digital signal processing, and enables an offloading of processing load from the microcontroller. The DSP may be embodied in specialized integrated circuit(s) or as field programmable gate arrays (FPGAs). In one embodiment, the DSP comprises a pipelined architecture, which comprises a central processing unit (CPU), plural circular buffers and separate program and data memories according to a Harvard architecture. The DSP further comprises dual busses, enabling concurrent instruction and data fetches. The DSP may also comprise an instruction cache and I/O controller, such as those found in Analog Devices SHARC® DSPs, though other manufacturers of DSPs may be used (e.g., Freescale multi-core MSC81xx family, Texas Instruments C6000 series, etc.). The DSP is generally utilized for math manipulations using registers and math components that may include a multiplier, arithmetic logic unit (ALU, which performs addition, subtraction, absolute value, logical operations, conversion between fixed and floating point units, etc.), and a barrel shifter. The ability of the DSP to implement fast multiply-accumulates (MACs) enables efficient execution of Fast Fourier Transforms (FFTs) and Finite Impulse Response (FIR) filtering. Some or all of the DSP functions may be performed by the microcontroller. The DSP generally serves an encoding and decoding function in the wearable device 36. For instance, encoding functionality may involve encoding commands or data corresponding to transfer of information. Also, decoding functionality may involve decoding the information received from the sensors 38 (e.g., after processing by the ADC).

The microcontroller comprises a hardware device for executing software/firmware, particularly that stored in memory 44. The microcontroller can be any custom made or commercially available processor, a central processing unit (CPU), a semiconductor based microprocessor (in the form of a microchip or chip set), a macroprocessor, or generally any device for executing software instructions. Examples of suitable commercially available microprocessors include Intel'S® Itanium® and Atom® microprocessors, to name a few non-limiting examples. The microcontroller provides for management and control of the wearable device 36.

The memory 44 (also referred to herein as a non-transitory computer readable medium) can include any one or a combination of volatile memory elements (e.g., random access memory (RAM, such as DRAM, SRAM, SDRAM, etc.)) and nonvolatile memory elements (e.g., ROM, Flash, solid state, EPROM, EEPROM, etc.). Moreover, the memory 44 may incorporate electronic, magnetic, and/or other types of storage media. The memory 44 may be used to store sensor data over a given time duration and/or based on a given storage quantity constraint for later processing.

The software in memory 44 may include one or more separate programs, each of which comprises an ordered listing of executable instructions for implementing logical functions. In the example of FIG. 2, the software in the memory 44 includes a suitable operating system and the application software 46, which in one embodiment, comprises sensor measurement communications capabilities via modules 48 and 50, respectively.

The operating system essentially controls the execution of computer programs, such as the application software 46 and associated modules 48, 50, and provides scheduling, input-output control, file and data management, memory management, and communication control and related services. The memory 44 may also include user data, including weight, height, age, gender, goals, body mass index (BMI) that may be used by the microcontroller executing executable code to accurately interpret the measured parameters. The user data may also include historical data relating past recorded data to prior contexts, including sleep history, driving history, etc. In some embodiments, user data may be stored elsewhere (e.g., at the mobile devices 24, 32 (FIG. 1), the vehicle processing unit 12 (FIG. 1), or remotely (e.g., in a storage device in the cloud(s) 18, 26 (FIG. 1).

The software in memory 44 comprises a source program, executable program (object code), script, or any other entity comprising a set of instructions to be performed. When a source program, then the program may be translated via a compiler, assembler, interpreter, or the like, so as to operate properly in connection with the operating system. Furthermore, the software can be written as (a) an object oriented programming language, which has classes of data and methods, or (b) a procedure programming language, which has routines, subroutines, and/or functions, for example but not limited to, C, C++, Python, Java, among others. The software may be embodied in a computer program product, which may be a non-transitory computer readable medium or other medium.

The input interface(s) 54 comprises one or more interfaces (e.g., including a user interface) for entry of user input, such as a button or microphone or sensor(s) (e.g., to detect user input, including as a touch-type display screen). For instance, the display screen may be embodied in one of several available technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMOLED), retina or haptic-based technology, or virtual/augmented reality technology. In some embodiments, the input interface 54 may serve as a communications port for downloaded information to the wearable device 36 (such as via a wired connection). The output interface(s) 56 comprises one or more interfaces for presenting feedback or data transfer (e.g., wired), including a user interface (e.g., display screen presenting a graphical or other type of user interface, virtual or augmented reality interface, etc.) or communications interface for the transfer (e.g., wired) of information stored in the memory 44. The output interface 56 may comprise other types of feedback devices, such as lighting devices (e.g., LEDs), audio devices (e.g., tone generator and speaker), and/or tactile feedback devices (e.g., vibratory motor) and/or electrical feedback devices.

Figure 3:
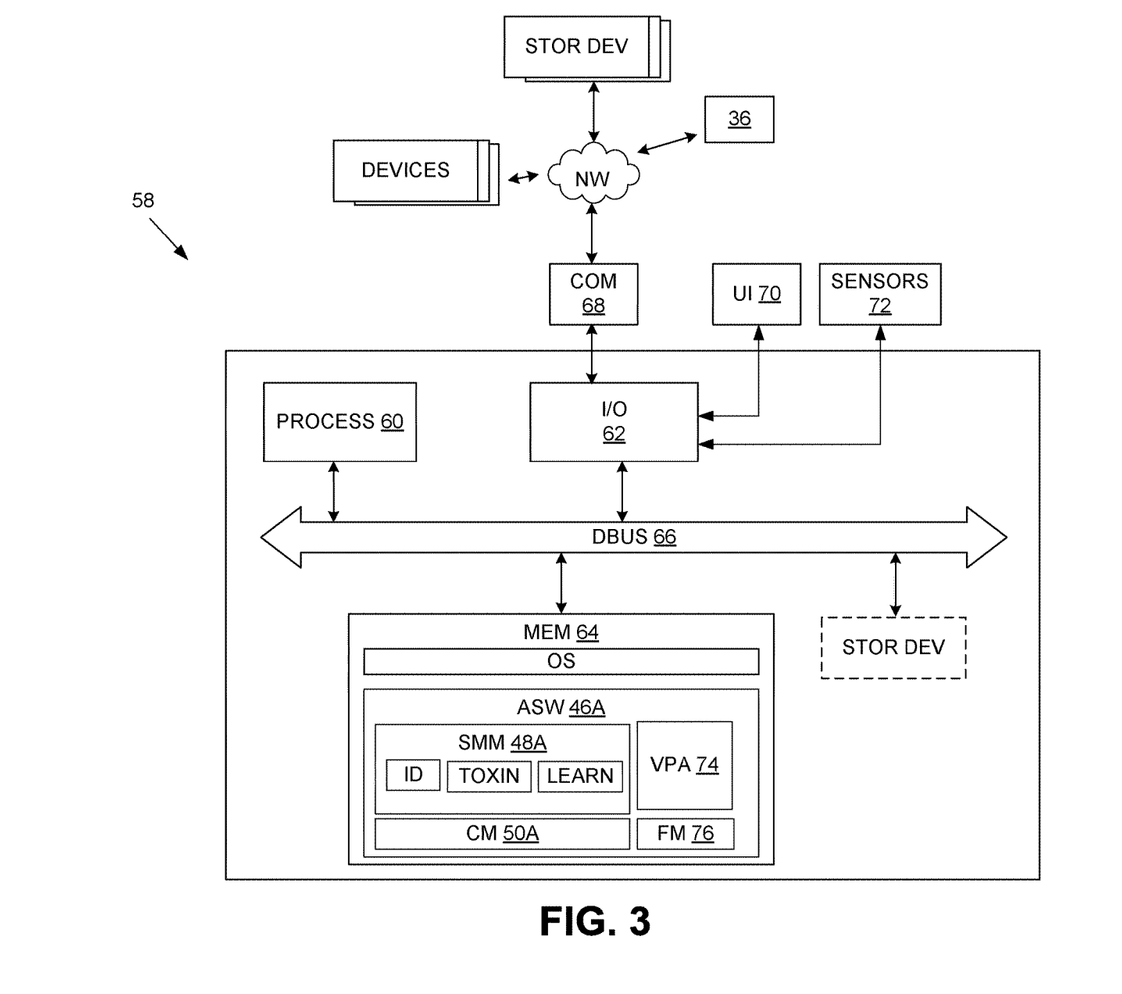
FIG. 3 is a schematic diagram that illustrates an example vehicle processing unit in which in which all or a portion of the functionality of a vehicle settings adjustment system may be implemented, in accordance with an embodiment of the invention.

Referring now to FIG. 3, shown is an embodiment of an example vehicle processing unit 58 in which in which all or a portion of the functionality of a vehicle settings adjustment system may be implemented. The vehicle processing unit 12 (FIG. 1) may comprise the functionality and structure of the vehicle processing unit 58 depicted in FIG. 3. Functionality of the vehicle processing unit 58 may be implemented alone, or in some embodiments, in combination with one or more additional devices. In one embodiment, the vehicle processing unit 58 may be embodied as a computer, though in some embodiments, may be embodied as an application server (e.g., if functionality of the vehicle settings adjustment system is implemented primarily remotely). One having ordinary skill in the art should appreciate in the context of the present disclosure that the example vehicle processing unit 58 is merely illustrative of one embodiment, and that some embodiments may comprise fewer or additional components. The vehicle processing unit 58 is depicted in this example as a computer system. It should be appreciated that certain well-known components of computer systems are omitted here to avoid obfuscating relevant features of the vehicle processing unit 58. In one embodiment, the vehicle processing unit 58 comprises hardware and software components, including one or more processors (one shown), such as processor (PROCESS) 60, input/output (I/O) interface(s) 62 (I/O), and memory 64 (MEM), all coupled to one or more data busses, such as data bus 66 (DBUS). The memory 64 (also referred to herein as a non-transitory computer readable medium) may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 64 may store a native operating system (OS), one or more native applications, emulation systems, or emulated applications for any of a variety of operating systems and/or emulated hardware platforms, emulated operating systems, etc. In some embodiments, one or more separate storage devices (STOR DEV) may be coupled to the data bus 66, and/or the vehicle processing unit 58 may be coupled to network storage (STOR DEV) via a network and communications functionality as described further below.

In the depicted embodiment, the vehicle processing unit 58 is coupled via the I/O interfaces 62 to a communications interface (COM) 68, a user interface (UI) 70, and one or more sensors 72. In some embodiments, the communications interface 68, user interface 70, and one or more sensors 72 may be coupled directly to the data bus 66. The communications interface 68 comprises hardware and software for wireless functionality (e.g., Bluetooth, near field communications, Wi-Fi, 802.11, etc.), enabling wireless communications with devices located internal to the vehicle 10 (FIG. 1), including the wearable device 36 (FIG. 2), mobile device(s) 24, 32 (FIG. 1), among other devices (e.g., camera 34, FIG. 1), and optionally wireless (or wired, e.g., via a controller area network (CAN) bus) communications with sensors 72 of the vehicle 10 that are located on the exterior of the vehicle 10. In one embodiment, the communications interface 68 further comprises cellular modem functionality to enable cellular communications to access computing functionality of the cloud(s) 18, 26 (FIG. 1), such as to access public or proprietary data structures (e.g., databases). For instance, a user profile (including in some embodiments, user preferences for one or more vehicle parameters) may be located in one or more devices of the cloud(s) 18, 26, and includes user data (e.g., age, gender, sleep history, drive history, activity history, etc. of the driver and/or passenger) and/or public statistics (e.g., road information, including traffic statistics (e.g., via WAZE or DOT web-sites), road geography/topology, injury/death statistics for the road(s), construction information, weather data, mapping/location services, etc.). In some embodiments, the weather data may be acquired via sensors located within (or located on the exterior of the vehicle 10), or via stand-alone devices found within the vehicle 10 and communicated to the vehicle processing unit 58, including through the use of a netamo device. In some embodiments, one or more of the information may be stored locally for a transitory period (e.g., in one or more of the storage devices and/or memory 64).

The I/O interfaces 62 may comprise any number of interfaces for the input and output of signals (e.g., analog or digital data) for conveyance of information (e.g., data) over various networks and according to various protocols and/or standards.

The user interface 70 comprises one or any combination of a display screen with or without a graphical user interface (GUI), heads-up display, keypad, vehicle buttons/switches/knobs or other mechanisms to enable the entry of user commands for the vehicle controls, microphone, mouse, etc., and/or output (e.g., feedback or other messaging to the driver and/or passenger and vehicle operating controls. For instance, adjustments of vehicle parameters may be preceded by a displayed message asking the user to authorize/confirm that the adjustment is permitted/acceptable, or in some embodiments, feedback of the adjustments may be presented, or in some embodiments, such adjustments may be performed in a manner that is transparent to the user. In some embodiments, confirmation of an identity of the user may be requested (e.g., prompting the user to confirm or deny the identification). In some embodiments, the user interface 70 comprises speakers and/or microphones, such as to provide verbal notification (e.g., of adjustments to vehicle parameters). The user interface 70 further includes vehicle operating controls that include motors and/or actuators, vibratory devices, heating elements, etc., which enable the activation and adjustment of vehicle devices/components based on the sensed vehicle parameters. Such controls may reside in and/or control a seat, mirror, internal environmental controls, audio and/or video playback device (e.g., DVD player, game controller, radio, etc.), among other vehicle features.

The sensors 72 comprise internal and external sensors (e.g., internal sensors 16 and external sensor 14, FIG. 1), including camera sensors (e.g., camera 34, FIG. 1) and/or position locating sensors (e.g., GNSS receiver). The sensors 72 may further include vehicle sensors that are associated with various components or structures of the vehicle, including angle sensors for mirror position determination, load (e.g., capacitive) sensors for determining weight of a user (e.g., located within or adjacent to the seat(s)), position sensors for determining seat position, temperature sensors (e.g., seat, interior, and/or exterior temperature sensing). In some embodiments, these vehicle sensors may provide for closed-loop control of adjustments to the vehicle parameters (and hence adjustment to motors, actuators, etc. that enable adjustment of the vehicle parameters). In some embodiments, adjustments may be achieved via open loop control, where one or more of the aforementioned vehicle sensors are omitted. Other types of sensors 72 may include vehicle inertial motion sensors (e.g., gyroscopes, magnetometers), vehicle velocity sensors, and/or vehicle acceleration sensors. In some embodiments, one or more functionality of the sensors 72 may instead be achieved with sensors 38 (FIG. 2) of the wearable device 36, or used in conjunction with one or more of the sensors 38 of the wearable device 36 in some embodiments, or used in lieu of one or more of the sensors 38 of the wearable device 36 in some embodiments.

In the embodiment depicted in FIG. 3, the memory 64 comprises an operating system (OS) and application software (ASW) 46A. Note that in some embodiments, the application software 46A may be implemented without the operating system. In one embodiment, the application software 46A comprises a sensor measurement module 48A having in some embodiments, an identification module, toxins module, and learning module similar to that described above for the wearable device applications software 46 (FIG. 2), a communications module 50A, and further including a vehicle parameter adjust (VPA) module 74 and a feedback module (FM) 76. Note that in some embodiments, functionality of one or more of the modules of the application software 46A may be implemented in other devices (e.g., the wearable device 36 or in one or more devices of the cloud(s) 18, 26 (FIG. 1). In some embodiments, functionality of the application software 46A may be distributed among plural devices.

The sensor measurement module 48A receives raw or derived parameters from the sensors 72 and/or wearable device 36 (FIG. 2, and/or other devices) via the communications module 50A and formats for use in the modules 48A-76. In some embodiments, functionality of the sensor measurement module 48A may reside at the sensors 72 and/or sensors of the wearable device 36 (and/or other devices) and be received at the communications module 50A in a format suitable for processing, in which case the sensor measurement module 48A may be omitted. In some embodiments, the identification module of the sensor measurement module 48A may receive the physiological parameter(s) from the wearable device 36 (e.g., corresponding to an iris scan, fingerprint scan, and/or voice recording) and/or other sensors 72 and, using known algorithms, determine the identity of the user. The identity is then used by the vehicle processing unit 58 to trigger adjustments to one or more vehicle parameters. As indicated above, in some embodiments, the identification function may be performed at the wearable device 36. In some embodiments, the toxins module of the sensor measurement module 48A enables the determination of whether the user's ability to drive the vehicle 10 (FIG. 1) has been compromised (e.g., impaired due to alcohol or other toxins) based on data from one or more sensors 38 (FIG. 2) of the wearable device 36 and/or from other sensors 72. The determination is then used by the vehicle processing unit 58 to trigger adjustments to one or more vehicle parameters (e.g., disable the vehicle). In some embodiments, as explained above, the wearable device 36 may implement this determining function.

In some embodiments, the learning module of the sensor measurement module 48A may learn various patterns of behavior of the user based on data received from sensors the wearable device 36, sensors 72, and/or other sources (e.g., from the cloud(s) 18,26 (FIG. 1). Based on the learning, the learning module may predict certain actions of the user. For instance, assume a user works out regularly at a local gym. The learning module of the sensor measurement module 48A may recognize that the user is at the gym on a given date (e.g., based on GPS data and/or other data, including calendar data, social media information, mapping services, etc.), and determines that the user has probably worked out because the car was parked there for longer than a particular time period (e.g., 20 minutes). The learning module of the sensor measurement module 48A may also receive ambient temperature measurements (e.g., from sensors 72 and/or from the Internet) as well as real-time heart rate measurements (e.g., communicated directly by the wearable device 36, indirectly via a mobile device of the user, or accessed from the cloud(s) 18, 26 (e.g., based on regular uploads to a server-client activity tracker from the wearable device 36), where the vehicle processing unit 58 determines that the heart rate is gradually returning to resting heart rate. Accordingly, the learning module of the sensor measurement module 48A may signal the vehicle parameter adjustment module 74 to cause an increase in the ambient temperature within the vehicle 10 (via actuation of temperature controls of the user interface 70) (e.g., possibly in correlation to the decrease in heart rate). In some embodiments, the learning module of the sensor measurement module 48A may learn this post-workout preference over time, and the temperature may then be raised to that preferred temperature. In some embodiments, the prediction is based on one or any combination of physiological parameters or contextual parameters. As another example, assume the driver parks his vehicle 10 at the gym, and it is January and very cold outside. The learning module of the of the sensor measurement module 48A, in conjunction with the feedback module 76, may query the driver: "Would you like to warm the car via auto-start as you begin your cool-down in your workout?" The driver may select yes, and then proceed to go inside the gym and work out. After his heart rate has peaked and is gradually decreasing, the learning module of the sensor measurement module 48A (in conjunction with the communications interface 68 and communications module 50A) may receive the heart rate information (e.g., via direct or indirect receipt of signals from the wearable device 36 as explained in the prior example). The learning module of the sensor measurement module 48A may learn over time that once the driver's heart rate has peaked and decreased to a particular level, the driver typically gets in the car about 20 minutes later. Since it is January, the learning module of the sensor measurement module 48A may signal the vehicle parameter adjust module 74 to trigger an auto-start to begin warming up the car approximately 10 minutes before the normal time when the driver gets in the car based on its predictions from the data. If the driver's workout schedule is more erratic, then the learning module of the sensor measurement module 48A may learn that, too, and the "post gym workout" auto-start functionality will not be presented to the user as an option. As explained above, one or more of the functions in these examples may be implemented in the wearable device 36 (e.g., signaling when to start the vehicle 10 and/or when to activate the heating element), in the cloud(s) 18, 26, among other devices.

The communications module 50A, in coordination with the communications interface 68, receives the physiological parameters over a wireless (e.g., Bluetooth, NFC, Wi-Fi, optical coding, etc.) and/or wired medium (e.g., via a CAN bus). The communications functionality of the communications module 50A generally enables communications among devices connected to one or more networks (NW) (e.g., personal area network, local wireless area network, wide area network, cellular network, etc.), including enabling web-browsing and/or access to cloud services through the use of one or more APIs.

Execution of the application software 46A may be implemented by the processor 60 under the management and/or control of the operating system (or in some embodiments, without the use of the OS). The processor 60 (or processors) may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the vehicle processing unit 58.

Figure 4:
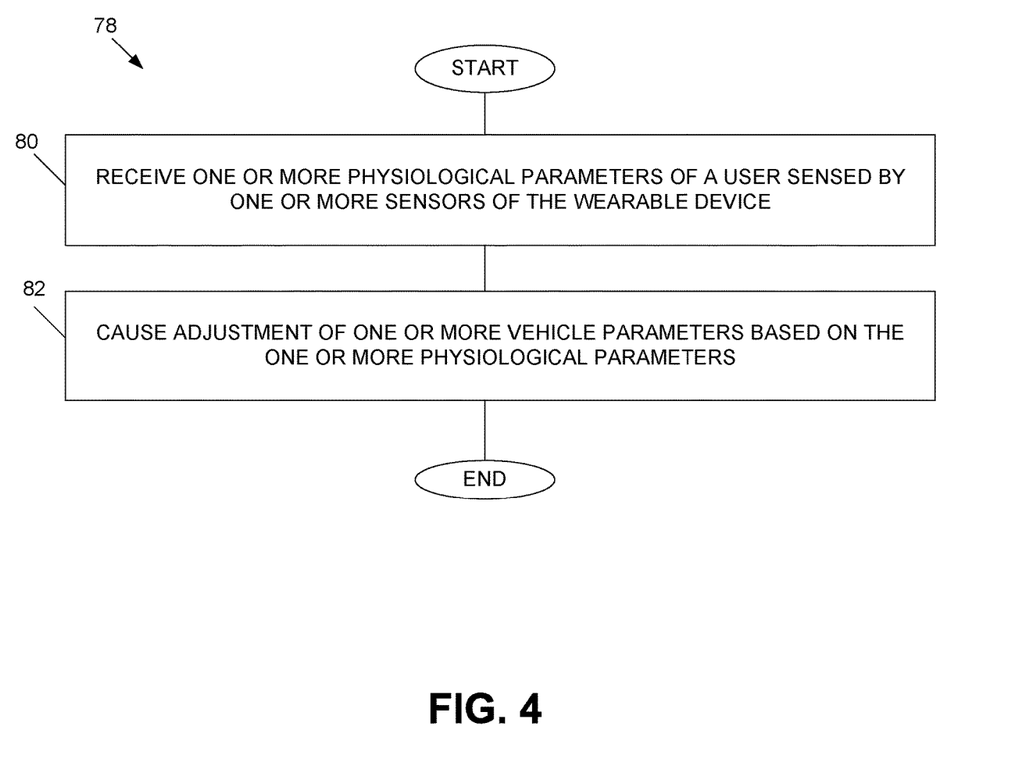
FIG. 4 is a flow diagram that illustrates an example vehicle occupant interaction method, in accordance with an embodiment of the invention.

When certain embodiments of the vehicle processing unit 58 are implemented at least in part with software (including firmware), as depicted in FIG. 4, it should be noted that the software can be stored on a variety of non-transitory computer-readable medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the vehicle processing unit 58 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

Having described some example architectures and functionality for certain devices of an example vehicle occupant interaction system, it should be appreciated that one method embodiment, depicted in FIG. 4 and denoted as method 78, comprises receiving one or more physiological parameters of a user sensed by one or more sensors of the wearable device (80); and causing adjustment of one or more vehicle parameters based on the one or more physiological parameters (82). Note that the method 78 may be implemented according to the application software 46 and/or 46A (FIGS. 2-3) of one or more devices, as executed by one or more processors. In one embodiment, the method 78 may be implemented on a non-transitory computer readable medium that is executed by one or more processors (e.g., in the same device or distributed among plural devices). Similarly, in some embodiments, the method 78 may be implemented within a single device (e.g., located within the vehicle 10 (FIG. 1) or located remote from the vehicle 10), or implemented by plural devices located within and/or external to the vehicle 10.

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure.

In an embodiment, a claim to a wearable device, comprising: one or more sensors; a memory comprising instructions; and one or more processors configured by the instructions to: receive one or more physiological parameters of a user sensed by the one or more sensors; and cause adjustment of one or more vehicle parameters based on the one or more physiological parameters.

In an embodiment, the wearable device according to the preceding claim, wherein the one or more processors are further configured by the instructions to: identify the user based on the sensed one or more physiological parameters, wherein the adjustment of the one or more vehicle parameters is based on pre-defined user settings.

In an embodiment, the wearable device according to any one of the preceding claims, wherein the one or more processors are further configured by the instructions to: receive a changed value for at least one of the one or more physiological parameters; and cause adjustment of the one or more vehicle parameters based on the changed value, the adjustment altering at least one of the pre-defined user settings.

In an embodiment, the wearable device according to any one of the preceding claims, wherein the one or more vehicle parameters are associated with passenger-focused settings or driver-focused settings.

In an embodiment, the wearable device according to any one of the preceding claims, wherein the one or more vehicle parameters, when adjusted, affect one or any combination of what the user feels, hears, sees, or the user's cognitive ability.

In an embodiment, the wearable device according to any one of the preceding claims, wherein the one or more vehicle parameters correspond to one or any combination of vehicle seat settings, mirror settings, interior climate settings, playback of one or a combination of video or audio playback, driving plan settings, or game console settings.

In an embodiment, the wearable device according to any one of the preceding claims, wherein the one or more sensors are configured to sense one or any combination of patterns in fingerprint, voice, iris, tongue, or ear of the user, and wherein the one or more processors are further configured by the instructions to: perform a scan of the one or any combination of patterns in fingerprint, voice, iris, tongue, or ear of the user; identify the user based on the scanned one or any combination of patterns in fingerprint, voice, iris, tongue, or ear of the user; and communicate the identity of the user to vehicle logic.

In an embodiment, the wearable device according to any one of the preceding claims, wherein the one or more physiological parameters comprise patterns in heart rate, heart rate variability, electrodermal activity, voice, facial features, fingerprint features, iris features, tongue features, ear features, respiration, activity, or sleep signals.

In an embodiment, the wearable device according to any one of the preceding claims, wherein the one or more processors are further configured by the instructions to interpret the one or more physiological parameters as an indication that the user's ability to operate a vehicle is compromised, and wherein the causing of the adjustment of the one or more vehicle parameters comprises preventing the vehicle from starting.

In an embodiment, the wearable device according to any one of the preceding claims, further comprising a communications module, wherein the one or more processors are further configured by the instructions to cause the communications module to communicate adjustments to another device.

In an embodiment, the wearable device according to any one of the preceding claims, wherein the one or more processors are further configured by the instructions to, prior to receiving and causing: receive a first set of physiological parameters; monitor changes to the one or more vehicle parameters; and correlate the changes to the one or more vehicle parameters to the first set of physiological parameters.

In an embodiment, a claim to a system, the system comprising: a vehicle processing unit; and a wearable device comprising one or more sensors, the wearable device configured to: sense one or more physiological parameters of a user; and communicate the one or more physiological parameters to the vehicle processing unit, wherein the vehicle processing unit is configured to cause an adjustment in one or more vehicle parameters based on the one or more physiological parameters.

In an embodiment, the system according to the preceding system claim, wherein the wearable device or the vehicle processing unit is further configured to: identify the user based on the sensed one or more physiological parameters, and wherein the vehicle processing unit is further configured to access pre-defined user settings for the identified user, wherein the adjustment of the one or more vehicle parameters is based on the pre-defined user settings.

In an embodiment, the system according to any one of the preceding system claims, wherein the wearable device is configured to sense a change in value to the one or more physiological parameters, wherein the vehicle processing unit is further configured to: receive the changed value; and cause adjustment of the one or more vehicle parameters based on the changed value, the adjustment altering at least one of the pre-defined user settings.

In an embodiment, the system according to any one of the preceding system claims, wherein the vehicle processing unit is further configured to, either prior to the adjustment based on the changed value or subsequent to the adjustment based on the changed value: prompt a message to the identified user.

In an embodiment, the system according to any one of the preceding system claims, wherein the one or more vehicle parameters correspond to one or any combination of vehicle seat settings, mirror settings, interior climate settings, playback of one or a combination of video or audio playback, driving plan settings, or game console settings.

In an embodiment, the system according to any one of the preceding system claims, further comprising one or more sensors configured to perform one or any combination of an iris scan, fingerprint scan, voice scan, tongue scan, or ear scan, and wherein the wearable device or vehicle processing unit is configured to identify the user based on the one or more scans, wherein the adjustment is based on the identification.

In an embodiment, the system according to any one of the preceding system claims, wherein the wearable device or vehicle processing unit is configured: predict, based on a learning algorithm, when the user will be in the vehicle, and wherein the causing of the adjustment of the one or more vehicle parameters comprises causing a change in environmental controls of the vehicle based on the prediction, the prediction further based on one or any combination of the physiological parameters or contextual information.

In an embodiment, the system according to any one of the preceding system claims, wherein the wearable device or the vehicle processing unit is further configured to interpret the one or more physiological parameters as an indication that the user's ability to operate a vehicle is compromised, and wherein the causing of the adjustment of the one or more vehicle parameters comprises preventing the vehicle from starting.

In an embodiment, a claim to a method implemented by a wearable device, the method comprising: receiving one or more physiological parameters of a user sensed by one or more sensors of the wearable device; and causing adjustment of one or more vehicle parameters based on the one or more physiological parameters.

Note that various combinations of the disclosed embodiments may be used, and hence reference to an embodiment or one embodiment is not meant to exclude features from that embodiment from use with features from other embodiments.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

At least the following is claimed:
1. A wearable device, comprising:
one or more sensors;
a memory comprising instructions; and
one or more processors configured by the instructions to:
receive one or more physiological parameters of a user sensed by the one or more sensors;
determine an identity of the user based on the one or more physiological parameters;
send the identity of the user to a processing unit in a vehicle;
cause the processing unit to access pre-defined user settings from a storage system based on the identity of the user; and
cause adjustment of one or more vehicle parameters based on the pre-defined user settings.

2. The wearable device of claim 1, wherein the one or more processors are further configured by the instructions to:
receive a changed value for at least one of the one or more physiological parameters; and
cause adjustment of the one or more vehicle parameters based on the changed value, the adjustment altering at least one of the pre-defined user settings.

3. The wearable device of claim 1, wherein the one or more vehicle parameters are associated with passenger-focused settings or driver-focused settings.

4. The wearable device of claim 1, wherein the one or more vehicle parameters, when adjusted, affect one or any combination of what the user feels, hears, sees, or the user's cognitive ability.

5. The wearable device of claim 1, wherein the one or more vehicle parameters correspond to one or any combination of vehicle seat settings, mirror settings, interior climate settings, playback of one or a combination of video or audio playback, driving plan settings, or game console settings.

6. The wearable device of claim 1, wherein the one or more sensors are configured to sense one or any combination of patterns in fingerprint, voice, iris, tongue, or ear of the user, and wherein the one or more processors are further configured by the instructions to:
perform a scan of the one or any combination of patterns in fingerprint, voice, iris, tongue, or ear of the user;
identify the user based on the scanned one or any combination of patterns in fingerprint, voice, iris, tongue, or ear of the user; and
communicate the identity of the user to vehicle logic.

7. The wearable device of claim 1, wherein the one or more physiological parameters comprise patterns in heart rate, heart rate variability, electrodermal activity, voice, facial features, fingerprint features, iris features, tongue features, ear features, respiration, activity, or sleep signals.

8. The wearable device of claim 1, wherein the one or more processors are further configured by the instructions to interpret the one or more physiological parameters as an indication that the user's ability to operate a vehicle is compromised, and wherein the causing of the adjustment of the one or more vehicle parameters comprises preventing the vehicle from starting.

9. The wearable device of claim 8, further comprising a communications module, wherein the one or more processors are further configured by the instructions to cause the communications module to communicate adjustments to another device.

10. The wearable device of claim 1, wherein the one or more processors are further configured by the instructions to, prior to receiving and causing:
receive a first set of physiological parameters;
monitor changes to the one or more vehicle parameters; and
correlate the changes to the one or more vehicle parameters to the first set of physiological parameters.

11. A method implemented by a wearable device, the method comprising:
receiving one or more physiological parameters of a user sensed by one or more sensors of the wearable device;
determining an identity of the user based on the one or more physiological parameters;
sending the identity of the user to a processing unit in a vehicle;
causing the processing unit to access pre-defined user settings from a storage system based on the identity of the user; and
causing adjustment of one or more vehicle parameters based on the pre-defined user settings.

12. A system, comprising:
one or more sensors;
a memory comprising instructions; and
one or more processors configured by the instructions to:
receive one or more physiological parameters of a user sensed by the one or more sensors;
send the one or more physiological parameters to a processing unit in a vehicle;
cause the processing unit to determine an identity of the user based on the one or more physiological parameters;
cause the processing unit to access pre-defined user settings from a storage system based on the identity of the user; and
cause adjustment of one or more vehicle parameters based on the pre-defined user settings.

13. The system of claim 12, wherein the system is a wearable device.

* * * * *